United States Patent
Grey

(10) Patent No.: US 7,365,217 B2
(45) Date of Patent: Apr. 29, 2008

(54) OXIDATION PROCESS

(75) Inventor: Roger A. Grey, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 187 days.

(21) Appl. No.: 11/338,999

(22) Filed: Jan. 25, 2006

(65) Prior Publication Data

US 2007/0173655 A1    Jul. 26, 2007

(51) Int. Cl.
    C07D 301/10    (2006.01)
    C07C 45/00     (2006.01)
    C07C 29/03     (2006.01)

(52) U.S. Cl. .................... 549/533; 568/403; 568/910; 568/399

(58) Field of Classification Search ............... 549/533; 568/357, 403, 910, 959, 399
    See application file for complete search history.

(56) References Cited

U.S. PATENT DOCUMENTS

| | | | |
|---|---|---|---|
| 2,911,452 A | 11/1959 | Broughton | 260/677 |
| 3,351,635 A | 11/1967 | Kollar | 260/348.5 |
| 3,449,219 A | 6/1969 | Schmidt | 203/68 |
| 3,450,055 A | 6/1969 | England | 103/51 |
| 3,464,897 A | 9/1969 | Jubin, Jr. | 203/52 |
| 3,580,819 A | 5/1971 | Hoory et al. | 203/42 |
| 4,038,322 A | 7/1977 | de Radzitzky d'Ostrowick et al. | 260/597 R |
| 4,110,501 A | 8/1978 | Tarbell et al. | 428/40 |
| 4,367,342 A | 1/1983 | Wulff et al. | 549/529 |
| 4,833,260 A | 5/1989 | Neri et al. | 549/531 |
| 4,859,798 A | 8/1989 | Lyons et al. | 568/399 |
| 4,918,238 A | 4/1990 | Costantini et al. | 568/342 |
| 4,978,799 A | 12/1990 | Sanderson et al. | 568/385 |
| 4,994,589 A | 2/1991 | Notermann | 549/534 |
| 5,126,491 A | 6/1992 | Clerici et al. | 568/342 |
| 5,235,111 A * | 8/1993 | Clerici et al. | 568/399 |
| 5,334,780 A | 8/1994 | Shaikh et al. | 568/910 |
| 5,345,010 A | 9/1994 | Lyons et al. | 568/910 |
| 5,354,857 A | 10/1994 | Ellis, Jr. et al. | 540/135 |
| 5,409,876 A | 4/1995 | Clerici et al. | 502/242 |
| 5,543,532 A | 8/1996 | Kourtakis et al. | 549/260 |
| 5,623,090 A | 4/1997 | Haruta et al. | 568/360 |
| 5,663,328 A | 9/1997 | Ellis, Jr. et al. | 540/145 |
| 5,780,657 A | 7/1998 | Cooker et al. | 549/534 |
| 5,856,534 A | 1/1999 | Cooker et al. | 549/534 |
| 5,973,171 A * | 10/1999 | Cochran et al. | 549/533 |
| 6,008,388 A | 12/1999 | Dessau et al. | 549/531 |
| 6,362,349 B1 | 3/2002 | Kuperman et al. | 549/533 |
| 6,498,259 B1 | 12/2002 | Grey et al. | 549/533 |
| 6,646,142 B1 | 11/2003 | Meima et al. | 549/536 |
| 6,646,158 B1 | 11/2003 | Karim et al. | 562/512.2 |
| 6,867,312 B1 | 3/2005 | Jubin, Jr. et al. | 549/523 |
| 6,914,029 B2 | 7/2005 | Davis et al. | 502/150 |
| 6,919,295 B2 | 7/2005 | Gaffney et al. | 502/311 |

FOREIGN PATENT DOCUMENTS

| | | |
|---|---|---|
| BE | 1001038 A7 | 6/1989 |
| EP | 0 126 488 | 5/1984 |
| EP | 0 345 856 | 5/1989 |
| JP | 4-352771 | 12/1992 |
| WO | WO 03/093202 | 11/2003 |
| WO | WO 2005/042449 | 5/2005 |

OTHER PUBLICATIONS

R. Szostak, Non-aluminosilicate Molecular Sieves in *Molecular Sieves Principles of Synthesis and Identification* (1989) 205.
G. Vayssilov, *Catal, Rev.—Sci. Eng.* 39(3) (1997) 209.
S. Hsu, *Hydrocarbon Process., Int. Ed*, 66(4) (1987) 43.
B. Liao et al., *Chem. Eng. J*, 84 (2001) 581.
V. Gokhale et al., *Ind. Eng. Chem. Res.* 34 (1995) 4413.
J. Labinger, *J. Mol. Catal. A: Chem.* 220 (2004) 27.
F. Cavani et al., "The Multifunctional Properties of Heterogeneous Catalysts, Active and Selective in the Oxidation of Light Paraffins," in *Studies in Surface Science and Catalysis 110: 3rd World Congress on Oxidation Catalysis* R. Grasselli et al. Ed. (1997) 19.
Q. Zhang et al., *J. Catal.* 202 (2001) 308.
G. Süss-Fink et al., *Appl. Catal. A* 217 (2001) 111.
P. Ratnasamy et al., *Stud. Surf. Sci. Catal.* 97 (1995) 367.
P. Ingallina et al., *Sci. Tech. Catal.* (1994) 31.
W. Sanderson, *Pure Appl. Chem.* 72 (7) (2000) 1289.
T. Tatsumi et al., *J. Chem. Soc., Chem. Commun.* (1992) 1446.

* cited by examiner

*Primary Examiner*—Bernard Dentz
*Assistant Examiner*—David E Gallis
(74) *Attorney, Agent, or Firm*—Yuanzhang Han

(57) ABSTRACT

A process is disclosed for reacting an olefin, hydrogen, and oxygen in a reactor in the presence of an epoxidation catalyst comprising a transition metal zeolite and a noble metal to produce a product stream comprising an epoxide and an alkane. The alkane is separated and oxidized to at least one oxygenated product.

23 Claims, No Drawings

OXIDATION PROCESS

FIELD OF THE INVENTION

The invention relates to a process for oxidizing an olefin with hydrogen and oxygen.

BACKGROUND OF THE INVENTION

Many different methods for the preparation of epoxides have been developed. Commercially, propylene oxide is produced by the chlorohydrin process or hydroperoxidation (see, e.g., U.S. Pat. Nos. 3,351,635 and 4,367,342; EP 0 345 856). Unfortunately, both processes have disadvantages. The chlorohydrin process suffers from the production of a dilute salt stream. The hydroperoxidation process, in which propylene is oxidized with an organic hydroperoxide such as ethylbenzene hydroperoxide or tert-butyl hydroperoxide, produces organic co-products such as t-butyl alcohol or styrene, whose value must be captured in the market place. Ethylene oxide is commercially produced by the direct oxidation of ethylene with oxygen over a silver catalyst. Unfortunately, efforts to epoxidize higher olefins (olefins containing three or more carbons) such as propylene with oxygen in the presence of a silver catalyst have failed to produce a commercial process (see, e.g., U.S. Pat. Nos. 5,856,534, 5,780,657 and 4,994,589).

Recent efforts have focused on the direct epoxidation of higher olefins with oxygen and hydrogen. For example, the reaction may be performed in the presence of a catalyst comprising gold and a titanium-containing support (see, e.g., U.S. Pat. Nos. 5,623,090, 6,362,349, and 6,646,142), or a catalyst containing palladium and a titanium zeolite (see, e.g., JP 4-352771).

Mixed catalyst systems for olefin epoxidation with hydrogen and oxygen have also been disclosed. For example, Example 13 of JP 4-352771 describes the use of a mixture of titanosilicate and Pd-on-carbon for propylene epoxidation. U.S. Pat. No. 6,008,388 describes a catalyst comprising a noble metal and a titanium or vanadium zeolite, but additionally teaches that the Pd can be incorporated into a support before mixing with the zeolite. The catalyst supports disclosed include silica, alumina, and activated carbon. U.S. Pat. No. 6,498,259 discloses the epoxidation of an olefin with hydrogen and oxygen in a solvent containing a buffer in the presence of a catalyst mixture containing a titanium zeolite and a noble metal catalyst.

Unfortunately, undesirable reactions also occur in these epoxidation processes. For example, the olefin can be hydrogenated to the corresponding alkane (U.S. Pat. No. 6,867,312). It would be desirable to convert the alkane formed from the epoxidation process to more valuable oxygenated products.

SUMMARY OF THE INVENTION

This invention is a process comprising reacting an olefin, hydrogen, and oxygen in the presence of an epoxidation catalyst comprising a transition metal zeolite and a noble metal to produce a product stream comprising an epoxide and an alkane. The process also comprises separating the alkane from the product stream and oxidizing it to produce at least one oxygenated product.

DETAILED DESCRIPTION OF THE INVENTION

The process of the invention include an epoxidation step. The epoxidation step comprises reacting an olefin, hydrogen, and oxygen in a reactor in the presence of an epoxidation catalyst comprising a transition metal zeolite and a noble metal to produce a product stream comprising an epoxide and an alkane. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. A transition metal is a Group 3-12 element. The first row of them includes elements from Sc to Zn. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed depends upon a number of factors, including the size and shape of the olefin to be epoxidized. For example, it is especially advantageous to use titanium silicalite-1 (TS-1, a titanium silicalite having an MFI topology analogous to that of the ZSM-5 aluminosilicate) for the epoxidation of propylene. For a bulky olefin such as cyclohexene, larger pore zeolites may be preferred.

Suitable titanium zeolites include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification*, (1989), Van Nostrand Reinhold, pp. 205-282). Small amounts of impurities, e.g., boron, iron, aluminum, phosphorous, copper, and the like, and mixtures thereof, may be present in the lattice. The amount of impurities is preferably less than 0.5 weight percent (wt. %), more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.* 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, and ZSM-12 are also suitable for use.

The epoxidation catalyst also comprises a noble metal. Suitable noble metals include gold, silver, platinum, palladium, iridium, ruthenium, osmium, rhenium, rhodium, and mixtures thereof. Preferred noble metals are Pd, Pt, Au, Re, Ag, and mixtures thereof. While any of the noble metals can be utilized, either alone or in combination, palladium and gold are particularly desirable. Typically, the amount of noble metal present in the catalyst will be in the range of from 0.01 to 20 wt. %, preferably 0.1 to 5 wt. %.

The noble metal and the transition metal zeolite may be on a single particle or on separate ones. For example, the noble metal may be supported on the transition metal zeolite. Alternatively, the epoxidation catalyst comprises a mixture of a transition metal zeolite and a noble metal, wherein the noble metal may be essentially elemental (e.g., colloidal Pd), or it may be supported on a carrier. Suitable carriers for the supported noble metal include carbon, titania, zirconia, niobia, silica, alumina, silica-alumina, titania-silica, zirconia-silica, niobia-silica, ion-exchange resins, and the like, and mixtures thereof.

The manner in which the noble metal is incorporated in the epoxidation catalyst is not critical. For example, the noble metal may be supported on the transition metal zeolite or other carriers by impregnation, ion exchange, adsorption, precipitation, or the like.

There are no particular restrictions regarding the choice of the noble metal compound or complex used as the source of the noble metal. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine)palladium(0)).

Similarly, the oxidation state of the noble metal is not critical. Palladium, for instance, may be in an oxidation state anywhere from 0 to +4 or any combination of such oxidation states. To achieve the desired oxidation state or combination of oxidation states, the noble metal compound after being introduced into the epoxidation catalyst may be fully or partially pre-reduced. Satisfactory catalytic performance can, however, be attained without any pre-reduction.

The weight ratio of the transition metal zeolite:noble metal is not particularly critical. However, a transition metal zeolite:noble metal weight ratio of 0.01-100 (grams of transition metal zeolite per gram of noble metal) is preferred.

The epoxidation catalyst is preferably in the form of a suspension or fixed-bed. The epoxidation step may be performed in a continuous flow, semi-batch, or batch mode. It is advantageous to work at a pressure of 1-200 bars. The epoxidation step is carried out at a temperature effective to achieve the desired olefin epoxidation, preferably at temperatures in the range of 0-200° C., more preferably, 20-150° C. Preferably, at least a portion of the reaction mixture is a liquid under the reaction conditions.

An olefin is required in the epoxidation step. Suitable olefins include any olefin having at least one carbon-carbon double bond, and generally from 2 to 60 carbon atoms. Preferably, the olefin is an acyclic alkene of from 2 to 30 carbon atoms. The process of the invention is particularly suitable for epoxidizing $C_2$-$C_6$ olefins. More than one double bond may be present in the olefin molecule, as in a diene or triene. The olefin may be a hydrocarbon or it may contain functional groups such as halide, carboxyl, hydroxyl, ether, carbonyl, cyano, nitro groups, or the like. The process of the invention is especially useful for converting propylene to propylene oxide.

Oxygen and hydrogen are also required. Although any sources of oxygen and hydrogen are suitable, molecular oxygen and molecular hydrogen are preferred. The molar ratio of hydrogen to oxygen can usually be varied in the range of $H_2$:$O_2$=1:100 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert gas is preferably used in the epoxidation step. Any desired inert gas can be used. Suitable inert gases include nitrogen, helium, argon, and carbon dioxide. Saturated hydrocarbons with 1-8, especially 1-6, and preferably 1-4 carbon atoms, e.g., methane, ethane, propane, and n-butane, are also suitable. Nitrogen and saturated $C_1$-$C_4$ hydrocarbons are preferred inert gases. Mixtures of inert gases can also be used. The molar ratio of olefin to gas is usually in the range of 100:1 to 1:10 and especially 20:1 to 1:10.

The amount of transition metal zeolite used may be determined on the basis of the molar ratio of the transition metal contained in the transition metal zeolite to the olefin that is supplied per unit time. Typically, sufficient transition metal zeolite is present to provide a transition metal/olefin per hour molar feed ratio of from 0.0001 to 0.1.

The epoxidation step preferably uses a solvent. Suitable solvents are liquid under the reaction conditions. They include, for example, oxygen-containing hydrocarbons such as alcohols, aromatic and aliphatic solvents such as toluene and hexane, chlorinated aromatic and aliphatic solvents such as chlorobenzene and methylene chloride, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, tert-butanol, and mixtures thereof. Fluorinated alcohols can be used.

It may be advantageous to use a buffer. The buffer is employed in the reaction to inhibit the formation of glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkyl-ammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphate, and ammonium hydroxide.

The epoxidation step produces a product stream comprising an epoxide and an alkane. The alkane is typically produced as a byproduct from the hydrogenation of the olefin. For example, if propylene is used as the olefin, propane may be formed in the epoxidation step as a byproduct.

The process of the invention includes a step for separating the alkane from the epoxidation product stream. For example, if propylene is used as the olefin, the product stream may contain propylene, propane, oxygen, hydrogen, inert gas (e.g., nitrogen), solvent, and other byproducts. Readily condensable components including propylene oxide, solvents (e.g., methanol, water), and heavy byproducts (e.g., glycol, glycol ethers) can be separated from the light materials comprised of propane, propylene, oxygen, hydrogen, and inert gases by evaporation or distillation. The mixture of propylene oxide, solvent, and heavy byproducts can be distilled to isolate propylene oxide. Similar separations are employed in other processes for making propylene oxide (see, e.g., U.S. Pat. Nos. 3,450,055, 3,464,897, 3,449, 219, 3,580,819, and 5,973,171). The light materials (propane, propylene, oxygen, hydrogen, and inert gases) can be separated into a $C_3$ stream (propylene and propane) and a lighter stream (oxygen, hydrogen, and inert gases) (see U.S. Pat. No. 5,973,171). Propane and propylene separation may be carried out by distillation, preferably at a pressure of from 50 to 400 psig. More preferably, the distillation is done at a pressure of from 250 to 350 psig. For other methods of separating propane and propylene, see, *Hydrocarbon Process.*, Int. Ed. 66(4) (1987) 43; *Chem. Eng. J.* 84(3) (2001) 581; *Ind. Eng. Chem. Res.* 34(12) (1995) 4413; WO 2003/093202; WO 2005/042449. Propane separated from the product steam may contain small amount of propylene (e.g., less than 5 wt. %, more preferably less than 1 wt. %, and most preferably less than 0.1 wt. %).

The separation of other alkanes from the corresponding olefins may be accomplished similarly. In the epoxidation of 1-butene, for example, a mixture of 1-butene and n-butane is obtained. n-Butane may be separated from 1-butene by distillation (see, e.g., U.S. Pat. No. 2,911,452).

The process of the invention also includes an oxidation step. This step comprises oxidizing the alkane to at least one oxygenated product. Oxidation of alkanes is well known in the art (see *J. Mol. Catal. A: Chem.* 220 (1) (2004) 27; F. Canani and F Trifiro, "The Multifunctional Properties of Heterogeneous Catalysts, Active and Selective in the Oxidation of Light Paraffins," in *Studies in Surface Science and Catalysis* 110: $3^{rd}$ *World Congress on Oxidation Catalysis*, R. K. Grasseli, et al., Elsevier Science B.V. (1997) pp. 19-34).

Generally, the oxidation of an alkane occurs in the presence of an oxidizing reagent. Suitable oxidizing reagents include oxygen, hydrogen peroxide, organic hydroperoxides (e.g., tert-butyl hydroperoxide, ethylbenzene hydroperoxide, cumene hydroperoxide), peroxy acids (e.g., peroxyacetic acid), ozone, and the like. Due to its low cost, oxygen is a preferred oxidizing reagent. In particular, air may be used as the source of oxygen. Another preferred oxidizing reagent is hydrogen peroxide because its only byproduct is water.

Oxidation of alkanes can give a variety of oxygenated products, including alcohols (see, e.g., U.S. Pat. Nos. 4,918,238, 4,978,799, 5,235,111, 5,345,010, 5,354,857, 5,409,876, and 5,663,328), aldehydes (see, e.g., *J. Catal.*, 202(2) (2001) 308; *Appl. Catal., A* 217(1-2) (2001) 111; U.S. Pat. No. 4,859,798), ketones (e.g., *Appl. Catal., A* 217(1-2) (2001) 111; EP 0126488; U.S. Pat. Nos. 4,038,322, 5,235,111, and 5,409,876), carboxylic acids and anhydrides (see, e.g., U.S. Pat. Nos. 5,543,532, 5,663,328, 6,646,158, 6,919,295, and 6,914,029). Oxidation of propylene may produce isopropanol, acetone, propionaldehyde, acrolein, acrylic acid, propionic acid, and the like, and mixtures thereof. Under appropriate reaction conditions, oxidation of propane may give isopropanol, acetone, or a mixture of them. Oxidation of n-butane may produce 1-butanol, 2-butanol, methyl ethyl ketone, n-butylaldehyde, n-butyric acid, maleic acid, maleic anhydride, and the like, and mixtures thereof.

The oxidation of an alkane is preferably performed in the presence of an oxidation catalyst. An oxidation catalyst is any material that is capable of catalyzing the oxidation of an alkane. The oxidation catalyst typically comprises a transition metal. Suitable transition metals include elements in Groups 3 to 11. The first row of these metals includes Sc, Ti, V, Cr, Mn, Fe, Co, Ni, and Cu. The transition metal may be present in any suitable oxidation state as long as it is capable of catalyzing the reaction. Examples of suitable oxidation catalysts are: supported transition metals (see, e.g., U.S. Pat. Nos. 5,235,111, 5,409,876, and 5,623,090), transition metal salts (see, e.g., EP 0126488; U.S. Pat. Nos. 4,038,322 and 5,543,532), transition metal complexes (see, e.g., U.S. Pat. Nos. 4,918,238, 4,978,799, 5,354,857, and 5,663,328), transition metal oxides or supported transition metal oxides (see, e.g., U.S. Pat. No. 5,345,010), mixed metal oxides (see, e.g., U.S. Pat. Nos. 6,646,158 and 6,919,295), transition metal zeolites (see, e.g., *J. Catal.* 202 (2) (2001) 308; *Stud. Surf. Sci. Catal.*, 97 (1995) 367; *Sci. Tech. Catal.* (1994) 31; U.S. Pat. No. 5,126,491), heteropolyacids or polyoxometallates (see, e.g., *Appl. Catal., A* 217(1-2), (2001), 111; *Pure Appl. Chem.* 72(7) (2000) 1289; U.S. Pat. Nos. 4,859,798, 5,334,780, and 6,914,029), and mixtures thereof. The oxidation catalyst may be soluble, partially soluble, or essentially insoluble in the reaction mixture under the reaction conditions.

Preferably, the oxidation catalyst comprises a transition metal zeolite. Suitable transition metal zeolites for the epoxidation catalyst described above are applicable for the present oxidation catalyst.

In one particular example, the oxidation catalyst comprises a noble metal and a transition metal zeolite, wherein the oxidizing reagent comprises oxygen and hydrogen (see, e.g., *J. Chem. Soc., Chem. Comm.* (1992) 1446; *Sci. Tech. Catal.* (1994) 31). Suitable noble metals and transition metal zeolites for the epoxidation catalyst and its preparation methods described above are applicable for the present oxidation catalyst.

The oxidation catalyst is preferably in the form of a suspension or fixed-bed. The oxidation step may be performed in a continuous flow, semi-batch, or batch mode. It is advantageous to work at a pressure of 1-200 bars. The oxidation step according to the invention is carried out at a temperature effective to achieve the desired alkane oxidation, preferably at temperatures in the range of 0-200° C., more preferably, 20-150° C.

The oxidation step may use a solvent. Suitable solvents are liquid under the reaction conditions. They include, for example, oxygen-containing hydrocarbons such as alcohols, aromatic and aliphatic solvents such as toluene and hexane, chlorinated aromatic and aliphatic solvents such as chlorobenzene and methylene chloride, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, tert-butanol, and mixtures thereof. Fluorinated alcohols can be used.

The oxidation step is preferably carried out in the presence of an acid. An acid is used to improve the rate or the selectivity of the oxidation reaction. Suitable acids include hydrobromic acid, hydrochloric acid, phosphoric acid, nitric acid, sulfuric acid, carbonic acid, carboxylic acids (e.g., formic acid, acetic acid, propionic acid), and the like, and mixtures thereof.

Following examples merely illustrate the invention. Those skilled in the art will recognize many variations that are within the spirit of the invention and scope of the claims.

EXAMPLE 1

Pd/TS-1 Catalyst

A TS-1 sample prepared by following procedures disclosed in U.S. Pat. Nos. 4,410,501 and 4,833,260 is calcined at 550° C. in air. It contains 2.1 wt. % Ti and <0.1 wt. % C.

Spray dried TS-1 (80 wt. % TS-1 and 20 wt. % silica binder, particle size=35 micron, 12 g) is slurried in deionized water (24 g) and the pH is adjusted from 4.8 to 7.3 with 5 wt. % aqueous ammonium hydroxide. After mixing for 5 min, an aqueous tetraammine palladium dinitrate solution (containing 0.97 wt. % Pd, 1.22 g) is added with mixing over 1 min. The pH is then adjusted from 6.1 to 7.3 with 5 wt. % aqueous ammonium hydroxide and the slurry is agitated at 30° C. for 10 min. The pH is adjusted from 6.7 to 7.3 and agitated at 30° C. for 20 min. The pH is adjusted from 7.0 to 7.3 with 5 wt. % aqueous ammonium hydroxide. The slurry is filtered and the filter cake is washed three times by reslurrying it in deionized water (25 g) followed by filtration. The solids are then air dried overnight and dried in a vacuum oven at 50° C. for 6 h. The dried solids contain 0.1 wt. % Pd and 2.1 wt. % Ti.

The above material is calcined in air in an oven that is heated from 23 to 110° C. at a rate of 10° C./min and maintained at 110° C. for 2 h, then heated to 300° C. at a rate of 2° C./min and maintained at 300° C. for 4 h. The calcined solids (containing 0.1 wt. % Pd, 2.1 wt. % Ti, <0.1 wt. % C, <0.1 wt. % N, and <0.1 wt. % H) are transferred to a quartz tube, heated to 100° C. and treated with 5 vol. % hydrogen in nitrogen (flow rate, 100 mL/min) for 4 h. After the hydrogen treatment, nitrogen is passed through the solid for 1 h before it is cooled to 23° C. The Pd/TS-1 (Catalyst A) is recovered.

EXAMPLE 2

Epoxidation of Propylene

An ammonium phosphate buffer solution (0.1 M, pH 6) is prepared as follows. Ammonium dihydrogen phosphate (11.5 g) is dissolved in deionized water (900 g). Aqueous ammonium hydroxide (30 wt. % $NH_4OH$) is added to the solution until the pH reads 6 via a pH meter. The volume of the solution is then increased to exactly 1000 mL with additional deionized water.

A 300-mL stainless steel reactor is charged with Catalyst A (0.7 g), the buffer solution prepared above (13 g), and methanol (100 g). The reactor is then charged to 300 psig with a feed gas consisting of 2 volume percent (vol. %) hydrogen, 4 vol. % oxygen, 5 vol. % propylene, 0.5 vol. % methane, and the balance nitrogen. The pressure in the reactor is maintained at 300 psig via a back pressure regulator with the feed gases passed continuously through the reactor at 1600 mL/min (measured at 23° C. and 1 atmosphere pressure). In order to maintain a constant solvent level in the reactor during the run, the oxygen, nitrogen and propylene feeds are passed through a 2-L stainless steel vessel (saturator) preceding the reactor containing 1.5 L of methanol. The reaction mixture is heated to 60° C. while it is stirred at 1500 rpm. The gaseous effluent is analyzed by an online gas chromatograph (GC) every hour and the liquid analyzed by offline GC at the end of the 18 h run. The products formed include propylene oxide (PO), propane, and derivatives of propylene oxide such as propylene glycol, propylene glycol monomethyl ethers, dipropylene glycol, and dipropylene glycol methyl ethers. The catalyst productivity is 0.37 g POE/g cat/h. Propylene to POE selectivity is 68%. Propylene to propane selectivity is 32%. The catalyst productivity is defined as the grams of PO formed (including PO which is subsequently reacted to form PO derivatives) per gram of catalysts (Pd/TS-1) per hour. POE (mole) =moles of PO+moles of PO units in the PO derivatives. PO/POE=(moles of PO)/(moles of POE)×100. Propylene to POE selectivity=(moles of POE)/(moles of propane formed+moles of POE)×100. Propylene to propane selectivity=(moles of propane formed)/(moles of propane formed+moles of POE)×100.

EXAMPLE 3

Oxidation of Propane

A 100-mL Parr reactor equipped with a magnetic stirring bar is charged with Catalyst A (0.2 g), methanol (18 g), and deionized water (2 g). After the reactor is closed, propane (6 g) is added. The reactor is pressurized to 210 psig with hydrogen and to 1300 psig with a gas mixture containing 4% oxygen in nitrogen. The reactor is heated to 80° C. and kept at 80° C. for 2 h. The reaction mixture is cooled to 23° C. and analyzed by GC. It contains 0.028 wt. % isopropanol.

EXAMPLE 4

Oxidation of Propane in the Presence of HBr

The procedure of Example 3 is repeated except that an aqueous HBr solution (0.055 wt. %, 0.22 g) is also charged in the reactor. GC analysis shows that the mixture contains 0.16 wt. % isopropanol and 0.02 wt. % acetone at the end of the reaction.

EXAMPLE 5

Oxidation of Propane in the Presence of HBr and $H_3PO_4$

The procedure of Example 3 is repeated except that deionized water (1.5 g), an aqueous HBr solution (0.055 wt. %, 0.22 g), and an aqueous $H_3PO_4$ solution (85 wt. %, 0.52 g) are charged in the place of deionized water (2 g). GC analysis shows the mixture contains 0.09 wt. % isopropanol and 0.31 wt. % acetone at the end of the reaction.

EXAMPLE 6

Oxidation of Propane in the Presence of Oxo-TEMPO

The procedure of Example 3 is repeated except that an aqueous 4-oxo-TEMPO (4-oxo-2,2,6,6-tetramethyl-1-piperidinyloxy radical) solution (0.1 wt. %, 0.3 g) is also charged in the reactor. GC analyses show the mixture contains 0.08 wt. % isopropanol and 0.008 wt. % acetone at the end of the reaction.

Repeating the procedures of Examples 3-6 using propane isolated from the product stream of Example 2 shall provide similar results.

EXAMPLE 7

Pd/$Nb_2O_5$ Catalyst

Pd($NH_3$)$_4$$Br_2$ (0.8 g) is dissolved in deionized water (120 g) in a beaker. In a separate beaker, niobium oxide powder (obtained from Reference Metals, 25 g) is slurried in deionized water (80 g). The palladium salt solution is added to the niobium oxide while it is being stirred over a period of 10 min. The slurry is stirred at 23° C. for another 2 h. The solid material is separated by centrifugation and washed by reslurrying it in deionized water (80 g). The centrifugation and washing step is repeated 4 times. The solid material is dried in a vacuum oven at 1 torr at 50° C. The dried solid thus obtained contains 1.2 wt. % Pd, 1.6 wt. % Br, 67 wt. % Nb, and 0.4 wt. % N.

The dried solid is calcined in air by heating it from 23 to 110° C. at a rate of 10° C./min and maintaining the temperature at 110° C. for 2 h, then heating to 350° C. at a rate of 2° C./min and maintaining the temperature at 350° C. for 4 h. The calcined solid (Catalyst B) contains 1.1 wt. % Pd, 0.51 wt. % Br, 67 wt. % Nb, and <0.1 wt. % N.

EXAMPLE 8

Oxidation of Propane with Catalyst Mixture

A 100-mL Parr reactor equipped with a magnetic stir bar is charged with Catalyst B (0.1 g), TS-1 powder (2 wt % Ti, 0.2 g), methanol (18 g), and deionized water (2 g). After the reactor is closed, propane (6 g) is added. The reactor is pressurized to 210 psig with hydrogen and to 1300 psig with a gas mixture containing 4% oxygen in nitrogen. The reactor is heated to 80° C. and kept at 80° C. for 2 h. The reaction mixture is cooled to 23° C. and analyzed by GC. It contains 0.19 wt. % acetone and 0.02 wt. % isopropanol.

EXAMPLE 9

Oxidation of Propane with Catalyst Mixture in the Presence of HBr and $H_3PO_4$

The procedure of Example 8 is repeated except that deionized water (1.5 g), an aqueous HBr solution (0.055 wt. %, 0.22 g), and an aqueous $H_3PO_4$ solution (85 wt. %, 0.52 g) are charged in the place of 2 g of deionized water. GC analysis shows that the mixture contains 0.4 wt. % acetone and 0.044 wt. % isopropanol.

EXAMPLE 10

Oxidation of Propane with Hydrogen Peroxide

A 100-mL Parr reactor equipped with a magnetic stirring bar is charged with TS-1 (Ti=2.3 wt. %, 0.2 g), methanol (20 g), and aqueous hydrogen peroxide (30 wt. %, 0.4 g). The reactor is closed and purged with nitrogen. Propane (6 g) is added and the reactor is pressurized to 600 psig with nitrogen. The reactor is heated to 60° C. and allowed to react for 1.75 h. The reaction mixture is cooled to 23° C. and analyzed by GC. GC analysis shows that the mixture contains 0.36 wt. % isopropanol and 0.1 wt. % acetone.

I claim:

1. A process comprising:
   (a) reacting an olefin, hydrogen, and oxygen in the presence of a buffer and an epoxidation catalyst comprising a transition metal zeolite and a noble metal to produce a product stream comprising an epoxide and an alkane;
   (b) separating the alkane from the product stream; and
   (c) oxidizing the alkane to at least one oxygenated product.

2. The process of claim 1 wherein the noble metal is supported on the transition metal zeolite.

3. The process of claim 2 wherein the transition metal zeolite is a titanium zeolite.

4. The process of claim 1 wherein the noble metal is supported on a carrier.

5. The process of claim 4 wherein the carrier is selected from the group consisting of carbon, titania, zirconia, niobia, silica, alumina, silica-alumina, titania-silica, zirconia-silica, niobia-silica, ion-exchange resins, and mixtures thereof.

6. The process of claim 4 wherein the transition metal zeolite is a titanium zeolite.

7. The process of claim 1 wherein step (c) is performed in the presence of an oxidation catalyst.

8. The process of claim 7 wherein the oxidation catalyst comprises a transition metal zeolite.

9. The process of claim 8 wherein the oxidation catalyst further comprises a noble metal.

10. The process of claim 9 wherein the noble metal is supported on the transition metal zeolite.

11. The process of claim 10 wherein the transition metal zeolite is a titanium zeolite.

12. The process of claim 9 wherein the noble metal is supported on a carrier.

13. The process of claim 12 wherein the carrier is selected from the group consisting of carbon, titania, zirconia, niobia, silica, alumina, silica-alumina, titania-silica, zirconia-silica, niobia-silica, ion-exchange resins, and mixtures thereof.

14. The process of claim 12 wherein the noble metal is selected from the group consisting of palladium, platinum, gold, rhenium, silver, and mixtures thereof.

15. The process of claim 12 wherein the transition metal zeolite is a titanium zeolite.

16. The process of claim 7 wherein step (c) is performed in the presence of an oxidizing reagent.

17. The process of claim 16 wherein the oxidizing reagent comprises oxygen.

18. The process of claim 16 wherein the oxidizing reagent comprises hydrogen peroxide.

19. The process of claim 7 wherein step (c) is performed in the presence of an acid.

20. The process of claim 19 wherein the acid is selected from the group consisting of hydrobromic acid, hydrochloric acid, phosphoric acid, nitric acid, sulfuric acid, carbonic acid, formic acid, acetic acid, propionic acid, and mixtures thereof.

21. The process of claim 1 wherein the olefin is propylene and the alkane is propane.

22. The process of claim 21 wherein the propane is separated from propylene by distillation.

23. The process of claim 21 wherein the oxygenated product is isopropanol, acetone, or a mixture of them.

* * * * *